(12) United States Patent
Cragg

(10) Patent No.: US 7,534,256 B2
(45) Date of Patent: *May 19, 2009

(54) INTRALUMINAL STENT AND GRAFT

(75) Inventor: Andrew H. Cragg, Edina, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 462 days.

This patent is subject to a terminal disclaimer.

(21) Appl. No.: 11/047,126

(22) Filed: Jan. 31, 2005

(65) Prior Publication Data

US 2005/0131529 A1    Jun. 16, 2005

Related U.S. Application Data

(60) Continuation of application No. 10/087,320, filed on Mar. 1, 2002, now Pat. No. 6,849,086, which is a continuation of application No. 09/687,247, filed on Oct. 13, 2000, now Pat. No. 6,387,122, which is a continuation of application No. 09/251,964, filed on Feb. 16, 1999, now Pat. No. 6,174,328, which is a continuation of application No. 09/005,654, filed on Jan. 12, 1998, now abandoned, which is a continuation of application No. 08/478,181, filed on Jun. 7, 1995, now Pat. No. 5,766,237, which is a division of application No. 08/344,524, filed on Nov. 23, 1994, now Pat. No. 5,683,448, which is a continuation of application No. 08/025,957, filed on Mar. 3, 1993, now abandoned, which is a continuation-in-part of application No. 07/839,911, filed on Feb. 21, 1992, now Pat. No. 5,405,377.

(51) Int. Cl.
*A61F 2/06* (2006.01)

(52) U.S. Cl. ............... 623/1.13; 606/191; 606/195; 606/198; 606/108

(58) Field of Classification Search ........... 623/1.13; 606/108, 191, 195, 198
See application file for complete search history.

(56) References Cited

U.S. PATENT DOCUMENTS 3,868,956 A   3/1975   Alfidl et al.
3,878,565 A   4/1975   Sauvage (Continued)

FOREIGN PATENT DOCUMENTS

DE         3918736 A1    12/1990

(Continued)

OTHER PUBLICATIONS

Dotter et al., "Transluminal Expandable Nitinol Coil Stent Grafting: Preliminary Report," Technical Developments and Instrumentation, *Radiology*, vol. 147, pp. 259-260 (Apr. 1983).

(Continued)

*Primary Examiner*—Vy Q. Bui
(74) *Attorney, Agent, or Firm*—RatnerPrestia

(57) ABSTRACT

An intraluminal stent and graft includes a stent made of a continuous helix of zig-zag wire and loops which connect adjacent apices of the wire. The stent is compressible and self-expandable substantially to a pre-compressed configuration. The device also includes a graft secured to the stent and made of a suitable biocompatible material.

12 Claims, 3 Drawing Sheets

U.S. PATENT DOCUMENTS

| | | |
|---|---|---|
| 3,890,977 A | 6/1975 | Wilson |
| 3,996,938 A | 12/1976 | Clark, III |
| 4,149,911 A | 4/1979 | Clabburn |
| 4,306,318 A | 12/1981 | Mano et al. |
| 4,425,908 A | 1/1984 | Simon |
| 4,494,531 A | 1/1985 | Gianturco |
| 4,503,569 A | 3/1985 | Dotter |
| 4,512,338 A | 4/1985 | Balko et al. |
| 4,553,545 A | 11/1985 | Maass et al. |
| 4,560,374 A | 12/1985 | Hammerslag |
| 4,577,631 A | 3/1986 | Kreamer |
| 4,580,568 A | 4/1986 | Gianturco |
| 4,649,922 A | 3/1987 | Wiktor |
| 4,655,771 A | 4/1987 | Wallsten |
| 4,665,906 A | 5/1987 | Jervis |
| 4,665,918 A | 5/1987 | Garza et al. |
| 4,681,110 A | 7/1987 | Wiktor |
| 4,729,766 A | 3/1988 | Bergentz et al. |
| 4,732,152 A | 3/1988 | Wallsten |
| 4,733,665 A | 3/1988 | Palmaz |
| 4,739,762 A | 4/1988 | Palmaz |
| 4,762,128 A | 8/1988 | Rosenbluth |
| 4,768,507 A | 9/1988 | Fischell et al. |
| 4,772,264 A | 9/1988 | Cragg |
| 4,776,337 A | 10/1988 | Palmaz |
| 4,787,899 A | 11/1988 | Lazarus |
| 4,800,882 A | 1/1989 | Gianturco |
| 4,820,298 A | 4/1989 | Leveen et al. |
| 4,830,003 A | 5/1989 | Wolff et al. |
| 4,856,516 A | 8/1989 | Hillstead |
| 4,878,906 A | 11/1989 | Lindemann et al. |
| 4,886,062 A | 12/1989 | Wiktor |
| 4,913,141 A | 4/1990 | Hillstead |
| 4,922,905 A | 5/1990 | Strecker |
| 4,969,458 A | 11/1990 | Wiktor |
| 5,019,090 A | 5/1991 | Pinchuk |
| 5,035,706 A | 7/1991 | Gianturco et al. |
| 5,041,126 A | 8/1991 | Gianturco |
| 5,057,092 A | 10/1991 | Webster, Jr. |
| 5,067,957 A | 11/1991 | Jervis |
| 5,078,726 A | 1/1992 | Kreamer |
| 5,078,736 A | 1/1992 | Behl |
| 5,085,635 A | 2/1992 | Cragg |
| 5,104,404 A | 4/1992 | Wolff |
| 5,116,365 A | 5/1992 | Hillstead |
| 5,123,917 A | 6/1992 | Lee |
| 5,133,732 A | 7/1992 | Wiktor |
| 5,135,536 A | 8/1992 | Hillstead |
| 5,201,901 A | 4/1993 | Harada et al. |
| 5,242,451 A | 9/1993 | Harada et al. |
| 5,282,824 A | 2/1994 | Gianturco |
| 5,314,472 A | 5/1994 | Fontaine |
| 5,360,443 A | 11/1994 | Barone et al. |
| 5,405,377 A | 4/1995 | Cragg |
| 5,456,713 A | 10/1995 | Chuter |
| 5,484,444 A | 1/1996 | Braunschweiler et al. |
| 5,507,767 A | 4/1996 | Maeda et al. |
| 5,545,211 A | 8/1996 | An et al. |
| 5,562,697 A | 10/1996 | Christiansen |

FOREIGN PATENT DOCUMENTS

| | | |
|---|---|---|
| DE | 41 02 550 A1 | 8/1991 |
| DE | 42 22 380 A1 | 1/1994 |
| EP | 0 145 166 B1 | 6/1985 |
| EP | 0 411 118 A1 | 2/1991 |
| EP | 0 480 667 A1 | 4/1992 |
| EP | 0 508 473 A2 | 10/1992 |
| EP | 0 540 290 A2 | 5/1993 |
| FR | 1 602 513 | 1/1971 |
| GB | 1205743 | 9/1970 |
| GB | 2106190 A | 4/1983 |
| WO | WO 89/02755 | 4/1989 |
| WO | WO 91/07928 | 6/1991 |
| WO | WO 92/00043 | 1/1992 |

OTHER PUBLICATIONS

Schetky, "Shape-Memory Alloys," pp. 74-82.

K. Otsuka et al., "Shape-Memory Alloys-Pseudoelasticity," *Metals Forum*, vol. 4, No. 3, pp. 142-152. (1981).

Cragg et al., "Nonsurgical Placement of Aterial Endoprostheses: A New Technique Using Nitinol Wire," *Radiology*, vol. 147, No. 1, pp. 261-263 (Apr. 1983).

Cragg et al., "Percutaneous Arterial Grafting," *Radiology*, vol. 150, No. 1, pp. 45-49 (1984).

T. W. Duerig et al., "An engineer's Perspective of Pseudoelasticity," pp. 369-393.

Cragg et al., "Stents/Vascular Stents," *Interventional Radiology*, pp. 686-692 (1990).

D. D. Lawrence et al. "Percutaneous Endovascular Graft: An Experimental Evaluation" (Abstract), *Radiology*, May 1987, pp. 357-360.

European Search Report dated May 27, 1993 (from European Patent Application No. 93102673.6 which was published on Aug. 25, 1993 as European Patent Publication No. EP 0 556 850 A1).

European Search Report dated Aug. 4, 1997 (from European Patent Application No. 96112898.0 which was published on Dec. 27, 1996 as European Patent Publication No. EP 0 749 729 A2).

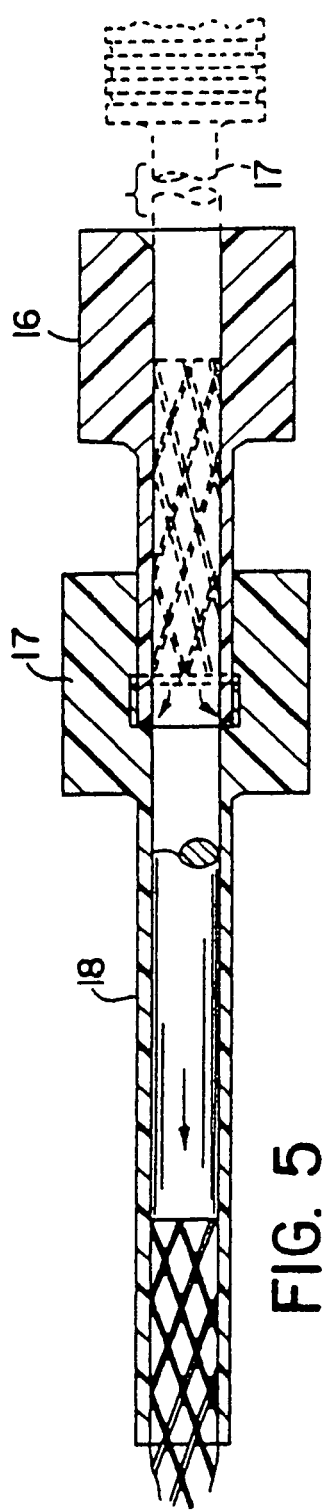
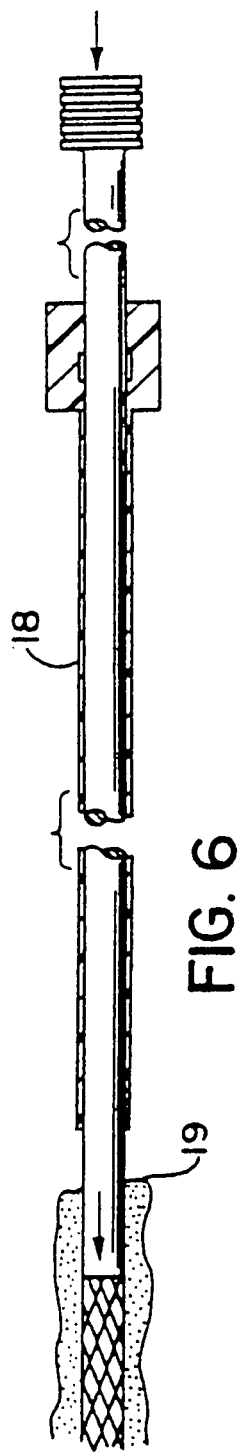
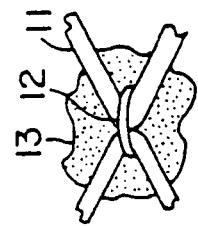
FIG. 9
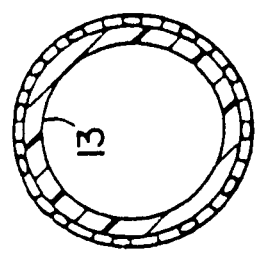
FIG. 8
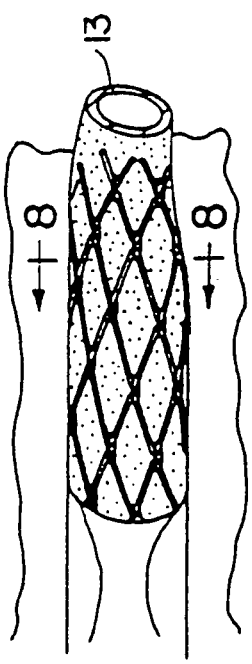
FIG. 7
FIG. 5
FIG. 6

INTRALUMINAL STENT AND GRAFT

This is a continuation of Ser. No. 10/087,320, filed Mar. 1, 2002, now U.S. Pat. No. 6,849,086 which is a continuation of application of U.S. application Ser. No. 09/687,247, filed Oct. 13, 2000, now U.S. Pat. No. 6,387,122 which is a continuation of U.S. application Ser. No. 09/251,964, filed Feb. 16, 1999, now U.S. Pat. No. 6,174,328 which is a continuation of U.S. application Ser. No. 09/005,654, filed Jan. 12, 1998, now abandoned which is a continuation of U.S. application Ser. No. 08/478,181, filed Jun. 7, 1995, now U.S. Pat. No. 5,766,237 which is a division of U.S. application Ser. No. 08/344,524, filed Nov. 23, 1994, now U.S. Pat. No. 5,683,448 which in turn is a continuation of U.S. application Ser. No. 08/025,957, filed Mar. 3, 1993, now abandoned which in turn is a continuation-in-part of U.S. application Ser. No. 07/839,911, filed Feb. 21, 1992 now U.S. Pat. No. 5,405,377.

BACKGROUND OF THE INVENTION

1. Field of the Invention

The present invention generally relates to a vascular prosthesis, and more particularly to an intraluminal stent which has a flexible and elastic tubular construction with sufficient hoop strength to prevent elastic recoil of balloon-resistant strictures or to produce delayed dilation of those strictures.

2. Description of the Prior Art

The prior art includes a wide variety of intraluminal stents and grafts. For example, Palmaz U.S. Pat. No. 4,733,665 discloses a balloon-expandable intraluminal graft, including an embodiment comprising a wire mesh tube. Intersecting wire members, secured to one another at their intersections by welding, soldering or gluing, form the wire mesh and define a diamond-like pattern. This structure provides a relatively high resistance to radial collapse; but it suffers a number of disadvantages. First it is a rigid structure which cannot easily assume the configuration of a curved vessel which receives it. Second one must us a balloon catheter to expand and implant it. This requirement limits the length of the graft, as does the rigidity.

Other prior stents have more flexible constructions; but they suffer other disadvantages. Wiktor U.S. Pat. No. 4,886,062, for example, discloses a stent which has a relatively flexible construction. This construction includes a deformable wire bent into a zig-zag design and coiled in a spiral fashion. The resulting wire tube has an open configuration with a reduced hoop strength. Each hoop lies essentially isolated from the adjacent hoops and does not obtain substantial support from them. Moreover, the open configuration increases the risk that plaque elements may herniate through the coil. Finally, one must use a balloon catheter to expand and implant it. Thus, the length of the stent cannot exceed the balloon length of available balloon catheters.

The intraluminal stent of the present invention avoids the disadvantages of the prior art stents and grafts. It has sufficient hoop strength to prevent elastic recoil of balloon-resistant strictures. The stent of the present invention has a flexible construction which allows it to follow the curvature of the vessel which receives it. It has an elastic construction which allows implantation without a balloon catheter. This elasticity further allows compression of the structure and recoil upon implantation to produce delayed dilation of the receiving vessel.

SUMMARY OF THE INVENTION

In accordance with an embodiment of the present invention, an intraluminal stent includes a predetermined length of wire having a sinuous or zig-zag configuration and defining a continuous helix with a plurality of connected spirals or hoops. A plurality of loop members connect adjacent apices of adjacent helix hoops. The stent is compressible and self-expandable substantially to the configuration prior to compression.

In accordance with an alternative embodiment of the present invention, an intraluminal stent includes the continuous helix and the plurality of loop members described above. It also includes a prosthetic graft disposed longitudinally of the wire helix within its central opening (or around the wire helix). One or more of the loop members secures the graft to the wire helix. This graft is a flexible, tubular shell which allows the wire helix to contract and recoil.

BRIEF DESCRIPTION OF THE DRAWINGS

For a more complete understanding of this invention one should now refer to the embodiments illustrated in greater detail in the accompanying drawings and described below by way of examples of the invention. In the drawings:

FIG. 5 is a sectional view of the devices used to implant the stent of FIG. 1;

FIG. 6 is a sectional view of the sheath and catheter devices used to implant the stent, showing the catheter holding the stent in place as the sheath moves out of the body vessel.

FIG. 7 is a side elevation view of an alternative embodiment of the stent of the present invention;

FIG. 8 is a sectional view taken along the line 8-8 in FIG. 7;

FIG. 9 is a partial perspective view of the stent of FIG. 7, showing a suture connection for the stent.

While the applicant will describe the invention in connection with preferred and alternative embodiments, one should understand that the invention is not limited to those embodiments. Furthermore, one should understand that the drawings are not necessarily to scale. In certain instances, the applicant may have omitted details which are not necessary for an understanding of the present invention.

The entire disclosure of U.S. patent application Ser. No 10/087,320 filed Mar. 1, 2002, is expressly incorporated by reference herein.

DETAILED DESCRIPTION OF THE DRAWINGS

Figure 1:
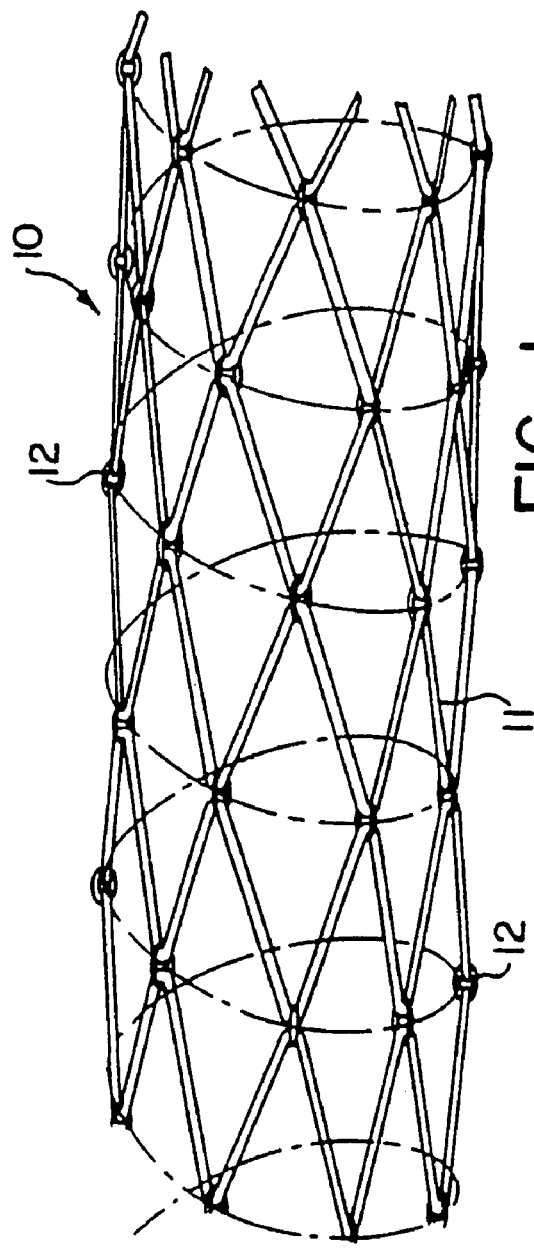
FIG. 1 is a perspective view of the intraluminal stent of the present invention.

Turning now to the drawings, FIG. 1 shows the intraluminal stent of the present invention generally at 10. This stent includes a wire body 11 made out of a predetermined length of wire having a sinuous or zig-zag configuration and defining a continuous helix with a series of connected spirals or hoops. It also includes loop members 12 which connect adjacent apices of adjacent helix hoops to help define the tubular stent. The loop members 12 may connect all or some of the pairs of adjacent apices.

The wire body 11 is an elastic alloy which provides radial elasticity for the stent. Preferably, it is a nitinol alloy which has superior elasticity and fatigue resistance. The wire has a round cross-section; but its cross-section may also be any one of a variety of shapes, e.g., triangular, rectangular, etc. Alternatively, any material of sufficient strength and elasticity and the other properties identified above may form the wire body, including stainless steel, tantalum, titanium, or any one of a variety of plastics.

Figure 4:
FIGS. 2-4 are side elevation view of a suture connection for the stent of FIG. 1.
Figure 3:
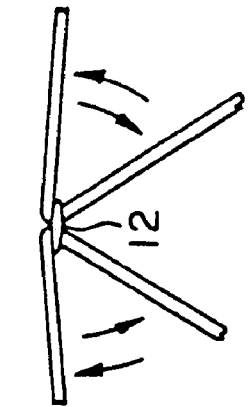
Figure 2:
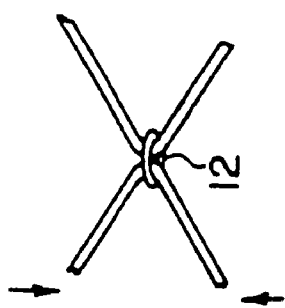

The loop members 12 connect adjacent apices of adjacent hoops of the wire body 11 so that the adjacent apices abut each other (See FIGS. 2-4). Thus, each hoop receives support from adjacent hoops, increasing the hoop strength of the overall stent structure and minimizing the risk of plaque herniation. The loop members 12 are ligatures of suture material with the ends tied together to form a loop. This material is polypropylene material or any other biocompatible material of sufficient strength. Although sutures are the preferred connecting means, other connecting means such as staples and rings made of metal or plastic may provide the same function.

The stent structure of the present invention allows compression prior to implantation in a human or animal vessel. After implantation, upon release of the compression force, the stent structure recoils (or self-expands) to its original configuration. Thus, it continues to provide dilating force in the implanted state. The structure provides flexibility which allows the stent to follow the curvature of the vessel which receives it.

Turning now to FIGS. 7-9, an alternative embodiment of the present invention includes the wire body and suture connections described above. This alternative also includes a prosthetic graft 13 disposed inside the central opening of the wire body. The graft is a round, open tube made of polytetrafluoroethylene (PTFF), dacron or any other suitable biocompatible material. One or more loop members 12 connect the graft 13 to the wire body 11 as shown in FIG. 9. In place, the graft closes the diamond shaped openings of the stent structure to further minimize plaque herniation and minimize the flow of fluid and cellular elements through the structure.

Alternatively, graft 13 may lie around the outside of the wire helix. Furthermore, the graft 13 may be co-extensive with the wire helix; or it may be shorter than the wire helix. Finally, the graft 13 may include a plurality of segments disposed within the wire helix or around the outside of the helix.

In one example, the graft 13 is a plain weave fabric construction made in a seamless tubular form on conventional equipment, either a shuttle narrow fabric weaving machine or a needle narrow fabric weaving machine. The tube is of multi filament polyester yarn of 40 denier or less (preferably 20, 30 or 40 denier). The wall thickness of the tube is 0.2 mm or less (preferably 0.1 mm); and it has a water permeability of between 50 and 500 ml/cm$^2$/min at 16 kPa (millimeters of water per square centimeter per minute at a pressure of 16 kPa). The fabric may be coated with a drug substance to reduce permeability, cause local anticoagulation, or reduce cellular infiltration.

Figure 10:
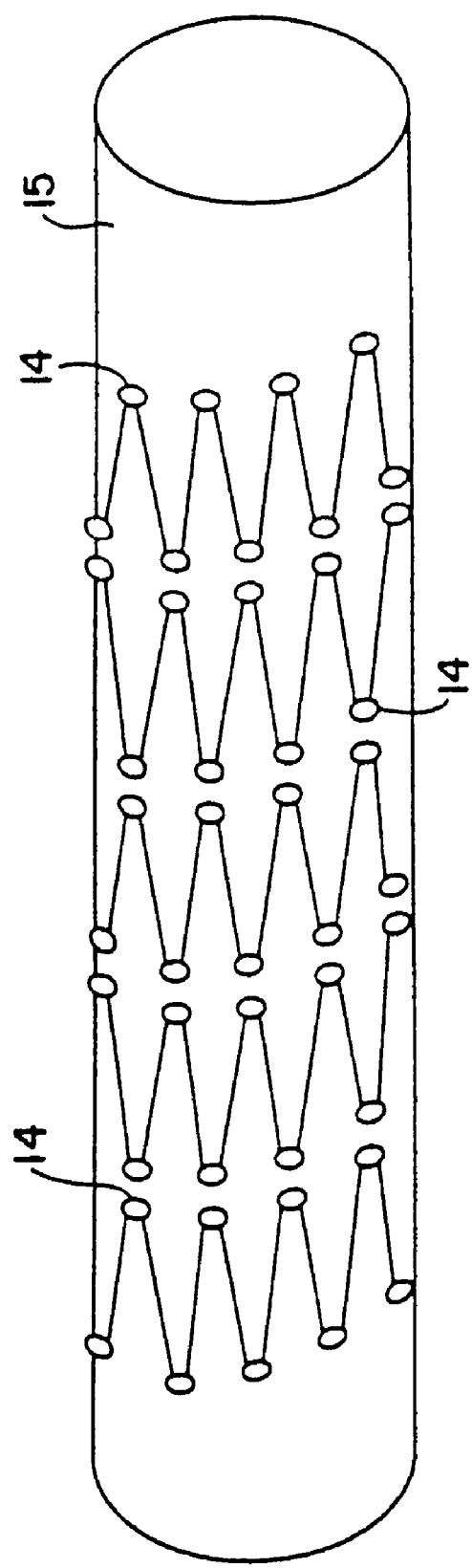
FIG. 10 is a perspective view of the mandrel used to form the wire helix of the present invention.

The method of making the stent of the present invention includes bending a predetermined length of wire in a zig-zag fashion between the pins 14 of the mandrel 15 and around the mandrel, thus forming a helix (See FIG. 10). The next step includes removing the helix from the mandrel by removing the pins and sliding the helix off the mandrel. The process further includes connecting adjacent apices of adjacent helix hoops. A fabricator makes each connection by placing a ligature of suture material (or any other suitable material) around the wire segments which define two adjacent apices and tying the ends of the ligature together to form a loop. In applications in which the wire body is nitinol wire, the process includes securing the ends of the wire to the mandrel and annealing the wire to a predetermined temperature (and thus imparting a thermal memory for the annealing shape) before removing the helix from the mandrel.

The method of implanting the stent and graft of the present invention includes compressing it and placing it into the central bore of an introducing device 16. The next step includes coupling the device 16 with the hub 17 of a sheath 18 which extends to the implantation location. The next step involves using a catheter 19 to push the compressed stent to the predetermined location with the catheter, and then removing the sheath. The final step involves removal of the catheter to allow the stent to recoil.

In applications in which the wire body is a nitinol metal, a user reduces the diameter of the stent by first cooling it, e.g., by submerging it in ice water. This cooling places the nitinol in a martensitic phase and facilitates manual reduction of the diameter and insertion of the stent in the central bore of the device 16. The device 16 and the sheath 18 restrain the stent until deployment in a predetermined location. At that location in a subject's body, body fluids warm the nitinol and place it in an austenitic phase which is the stable phase of this metal and which corresponds to a fully opened or expanded configuration of the stent (to its original annealed diameter).

While the above description and the drawings illustrate one embodiment and an alternative, one should understand, of course, that the invention is not limited to those embodiments. Those skilled in the art to which the invention pertains may make other modifications and other embodiments employing the principals of this invention, particularly upon considering the foregoing teachings. For example, one may use a deformable material to construct the wire body 11 of the stent and then use a balloon catheter to deploy it. The applicant, therefore, by the appended claims, intends to cover any modifications and other embodiments which incorporate those features which constitute the essential features of this invention.

What is claimed:

1. A stent-graft combination comprising a tubular stent having a plurality of hoops aligned adjacent one another along the axis of said tubular stent, each of said hoops comprising a plurality of elongate elements, with pairs of said elongate elements meeting one another and forming vertices axially pointing in a direction along the axis of the stent, wherein at least some of said vertices axially abut and are individually connected to oppositely pointed vertices of elongate elements of an adjacent hoop by separate connecting members which connect adjacent vertices so that they abut one another, further including a tubular graft member disposed circumferentially adjacent the tubular stent and wherein at least one elongate element from one hoop is continuous with a second elongate element of an adjacent hoop.

2. A stent-graft combination according to claim 1, wherein said stent is comprised of a shape memory material.

3. A stent-graft combination according to claim 2, wherein said shape memory material is nitinol.

4. A stent-graft combination according to claim 1, wherein said stent is comprised of an elastic material.

5. A stent-graft combination according to claim 4, wherein said elastic material is stainless steel.

6. A stent-graft combination according to claim 1, wherein said graft covers diamond shaped openings in said stent.

7. A stent-graft combination according to claim 1, wherein said graft covers diamond shaped openings in said stent and is attached to said stent by ligature loops.

8. A stent-graft combination according to claim 7, wherein said ligature loops also form connections between abutting apices of said stent.

9. A stent-graft combination according to claim 1, wherein the graft is disposed on an outer surface of the stent.

10. A stent-graft combination according to claim 1, wherein the graft is disposed on an inner surface of the stent.

11. A stent-graft according to claim 1, wherein said graft member includes a drug substance disposed thereon.

12. A stent-graft according to claim 1, wherein said graft comprises polyester or polytetrafluoroethylene.

* * * * *